United States Patent [19]

Stone et al.

[11] Patent Number: 5,458,749
[45] Date of Patent: Oct. 17, 1995

[54] DEVICE AND PROCESS FOR STAINING ELECTROPHORETIC GELS

[75] Inventors: Edwin M. Stone; Brian E. Nichols, both of Iowa City, Iowa

[73] Assignee: Univeristy of Iowa Research Foundation, Iowa City, Iowa

[21] Appl. No.: 236,967

[22] Filed: May 2, 1994

[51] Int. Cl.[6] .......................... G01N 27/26; G01N 27/447
[52] U.S. Cl. .................................... 204/180.1; 204/182.8; 204/299 R; 422/99
[58] Field of Search ............................. 204/299 R, 182.8, 204/182.7, 180.1; 436/86; 422/99

[56] References Cited

U.S. PATENT DOCUMENTS

| 4,317,710 | 3/1982 | Suzuki et al. | 204/299 R |
| 4,750,506 | 1/1988 | Olexa | 134/201 |
| 4,844,782 | 7/1989 | Hagerlid et al. | 204/180.1 |
| 5,047,129 | 9/1991 | Nardo | 204/182.8 |

FOREIGN PATENT DOCUMENTS

| 58-72049 | 4/1983 | Japan. |
| 62-52448 | 3/1987 | Japan. |
| 62-211561 | 9/1987 | Japan. |

*Primary Examiner*—Kathryn Gorgos
*Assistant Examiner*—John S. Starsiak, Jr.
*Attorney, Agent, or Firm*—Woodard, Emhardt, Naughton, Moriarty & McNett

[57] ABSTRACT

A process and apparatus are described herein which provide for the automated processing of electrophoresed gels having biological material thereon within a single processing chamber. The described apparatus is implemented by control sequencing software to stain process electrophoretic gels by contact with a series of recirculated solutions including fixing, rinsing, staining, and developing solutions.

22 Claims, 5 Drawing Sheets

DEVICE AND PROCESS FOR STAINING ELECTROPHORETIC GELS

BACKGROUND

The present invention relates generally to analytical techniques used in biochemistry, and more particularly to improved devices and methods for staining electrophoretic gels so as to visualize electrophoresed biological material within the gels.

Electrophoresis is a well known method for analyzing biological materials such as proteins and nucleic acids for various purposes, including for example the diagnosis of disease states in humans and other animals. Generally, electrophoresis involves depositing the biological material of interest on a buffer-wetted porous support medium and applying an electrical field across the support. Because components of the biological sample have varying charges and molecular weights, they migrate at different rates and can therefore be separated by the support.

Most electrophoresed biological materials cannot be immediately visualized within the support and must therefore be subjected to a staining procedure which visually differentiates support areas containing biological materials from those which do not. For example, the staining procedure can render biological materials darker, or lighter, than their surrounding support environment.

One highly useful staining procedure is known as the silver staining method, and involves contacting electrophoresed gels, particularly polyacrylamide gels, with a staining agent including a source of silver ions, and a developing agent including a reducing agent to reduce the silver ions to silver metal. The silver ions are preferentially bound to the biological materials, and thus when the gel is developed a silver pattern emerges from which the relative migration of biological materials can be ascertained. Additional information relative to silver staining and other staining protocols can be found by reference to literature on the subject, including for instance Bassam et al., *Analytical Biochemistry* 196, 80–83 (1991), and U.S. Pat. Nos. 4,434,234; 4,391,689; 4,575,452; 4,582,808; and 5,064,768.

The processing of electrophoretic gels by presently known and available means is, unfortunately, both a time consuming and labor intensive effort. Accordingly, there is a strong need for improved devices and methods for conveniently and quickly staining electrophoretic gels. It is to this need and demand that the present invention is addressed.

SUMMARY OF THE INVENTION

The present invention provides methods and apparatuses for staining electrophoresis gels. Generally speaking, the inventive embodiments involve the use of an apparatus which is implemented by control sequencing software to perform multiple-step staining processes upon electrophoresed gels in a single processing chamber and without necessitating any physical transferring of the gels during the procedure. A number of processing solutions are fed and drained from the chamber in a serial fashion by the software routine, preferably to at least rinse, fix, and stain the gels. While present in the processing chamber, each solution is recirculated to promote uniform contacting over all areas of the gel surface. Processes and apparatuses of the invention thus significantly reduce manual reagent and gel handling requirements and streamline the processing of electrophoresed gels to reproducably visualize the biological materials thereon.

One object of the present invention is to provide an automated apparatus and process for staining electrophoretic gels which reduces the need to manually handle reagent liquids.

Another object of the invention is to provide an automated apparatus and process for staining electrophoretic gels which contacts the gels with a number of processing solutions in a single chamber and thus minimizes gel handling or transfer requirements.

Another object of the invention is to provide an automated apparatus and process for silver staining polyacrylamide gels which quickly and reproducably enables visualization of biological materials on the gels.

These and other objects are achieved by preferred embodiments of the invention, one of which provides a software driven apparatus for staining electrophoretic gels. The apparatus of the invention has a liquid processing chamber sized to receive one or more electrophoretic gels, for instance chemically affixed to a supporting glass plate, having electrophoresed biological material deposited thereon. The liquid processing chamber is also adapted to contain a series of processing fluids in intimate contact with areas of the electrophoretic gels containing the biological material. The preferred apparatus further includes several fluid sources, including sources of a fixing solution, staining solution, and a rinsing solution. The fluid sources are each operable to begin and cease communication of solution to the liquid processing chamber. The liquid processing chamber is also provided with a drain having an open state for draining solutions from the chamber and a closed state in which solutions are retained in the chamber. The inventive apparatus further includes control sequencing software operable to control the fluid sources and the drain so as to serially contact the electrophoretic gels with the fixing solution, rinsing solution and staining solution.

Another preferred embodiment of the invention provides a process for staining of electrophoretic gels. In the process, one or more electrophoretic gels having electrophoresed biological material deposited thereon are placed into a liquid processing chamber sized to receive the electrophoretic gels, wherein the liquid processing chamber is adapted to contain a series of processing fluids in intimate contact with areas of the electrophoretic gels containing the biological material. First, second and third fluid sources are provided containing, respectively, a fixing solution, a staining solution, and a rinsing solution. The fluid sources are each operable to begin and cease communication of their respective solutions to the liquid processing chamber. A drain is provided in the liquid processing chamber and has an open state for draining solutions from the chamber and a closed state for retaining solutions within the liquid processing chamber. Software is also provided and is operable to control the various fluid sources and the drain so as to serially contact the electrophoretic gels with the fixing solution, rinsing solution and staining solution. In accordance with the invention, this software is initiated whereafter the electrophoretic gels are caused to be stained, rinsed and developed.

Still another preferred embodiment of the invention relates to a method for processing of electrophoretic gels. The method includes (i) placing one or more electrophoretic gels having electrophoresed biological material deposited thereon into a liquid processing chamber sized to receive the electrophoretic gels. Under the control of control sequencing software. The liquid processing chamber is filled with and then drained of (ii) a fixing solution, (iii) a rinsing solution, (iv) a staining solution, and (v) a rinsing solution. The chamber is then filled with (vi) a developing solution. Next, the chamber is (vii) drained of the developing solution, (viii) filled with and drained of a develop stop solution, and then (ix) filled with and drained of a rinsing solution. The solutions are preferably recirculated during residence in the chamber, and steps or cycles (ii)–(v) and (vii)–(ix) are advantageously carried out in response to the operation of control sequencing software.

Additional objects, advantages and embodiments of the present invention will be apparent from the following description.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As will now be described in detail, the inventive embodiments of the present invention involve the use of an apparatus which is implemented by control sequencing software to perform multiple-step staining processes upon electrophoresed gels in a single chamber and without necessitating any physical transferring of the gels during the procedure. The following described inventive embodiments include a processing chamber for receiving electrophoresed gels and a number of fluid sources from which processing solutions are automatically fed into the processing chamber in a serial fashion to rinse, fix, and stain the gels in response to control sequencing software which automatically directs the operation of the staining process. Each solution is recirculated within the processing chamber to ensure uniform contacting over all areas of the gel surface, and is then drained from the processing chamber upon completion of the cycle. Processes and apparatuses of the invention significantly reduce manual reagent and gel handling requirements. The inventive embodiments further streamline and render highly reproducable the processing of electrophoresed gels to visualize the biological materials thereon.

Biological materials subjected to electrophoresis processes typically include nucleic acids such as DNA or RNA, and proteins. DNA is a biological material of especial interest in the present invention, as electrophoresed DNA samples can be used in the diagnosis of various genetic disorders and in DNA sequencing protocols. As well, the staining of DNA-containing gels is a particularly sensitive process which is difficult to carry out in a reproducable fashion. The present invention provides excellent, reproducible staining of DNA gels and thus addresses long prevalent problems in DNA-related electrophoretic applications.

Figure 1:
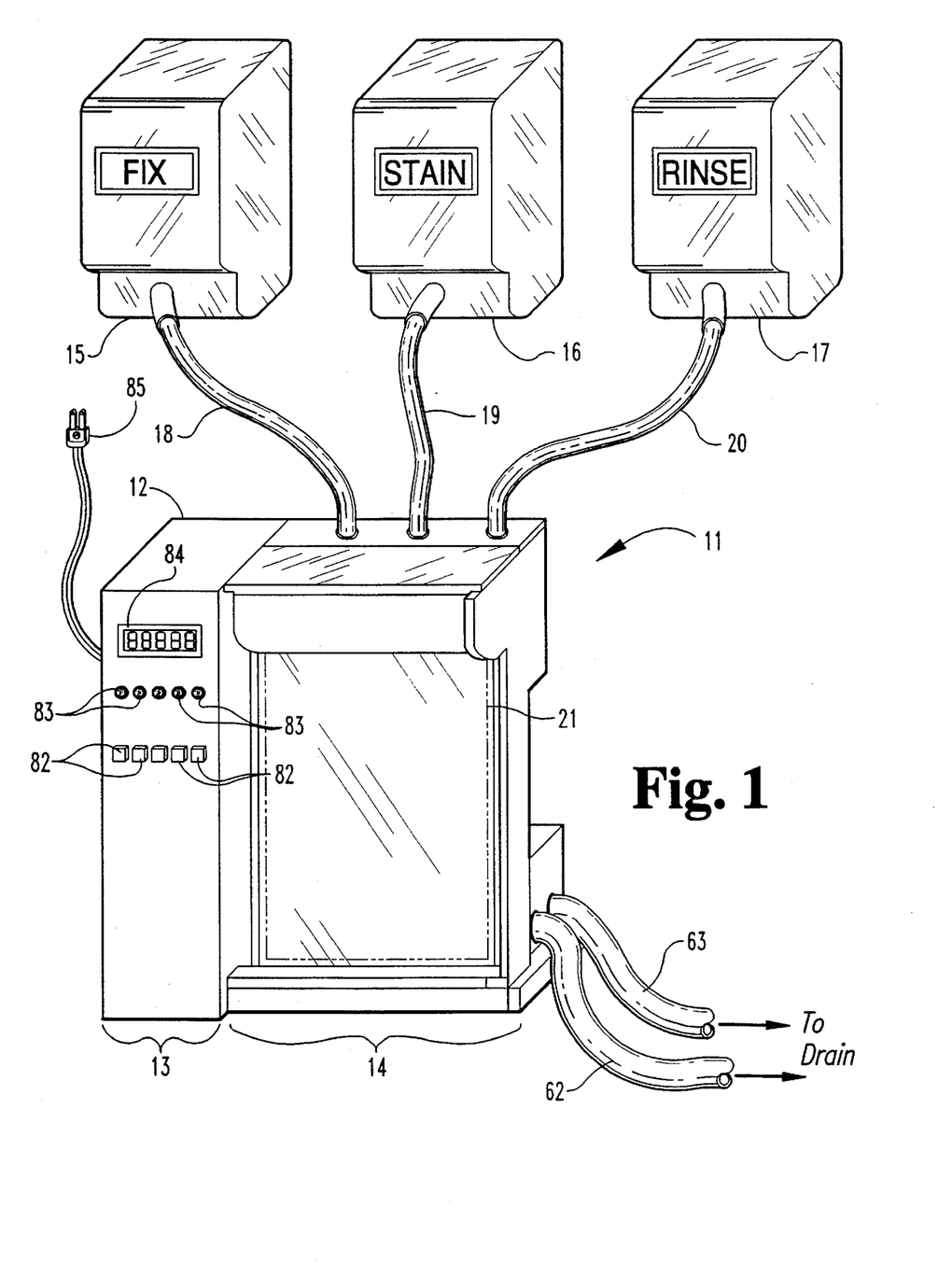
FIG. 1 provides a perspective view of a preferred automated staining apparatus of the present invention.

Referring now more particularly to FIG. 1, provided is a perspective view of a software-driven staining apparatus 11 of the present invention. Apparatus 11 includes a gel processing module 12 including an electronics box 13 and a liquid processing center 14. The various structural pieces forming processing module 12 described below are preferably constructed of a suitable plastic such as smoked or clear plexiglass, and can be bonded together with conventional adhesives or otherwise attached together, e.g. by screws and the like.

Containers of processing fluids are fluidly connected to liquid processing center 14 and include separate containers 15, 16 and 17 of fixing solution, staining solution and rinsing solution, respectively. This fluid connection is achieved through hoses 18, 19 and 20 which fluidly couple containers 15, 16 and 17, respectively, to liquid processing center 14. In the preferred apparatus 11, containers 15, 16 and 17 are provided generally above gel processing module 12 to enable gravity feed of the respective processing solutions to liquid processing center 14. As described in more detail below, apparatus 11 processes one or more electrophoresed gels 21 (shown in phantom, FIG. 1) to enable visualization of biological materials thereon.

Figure 2:
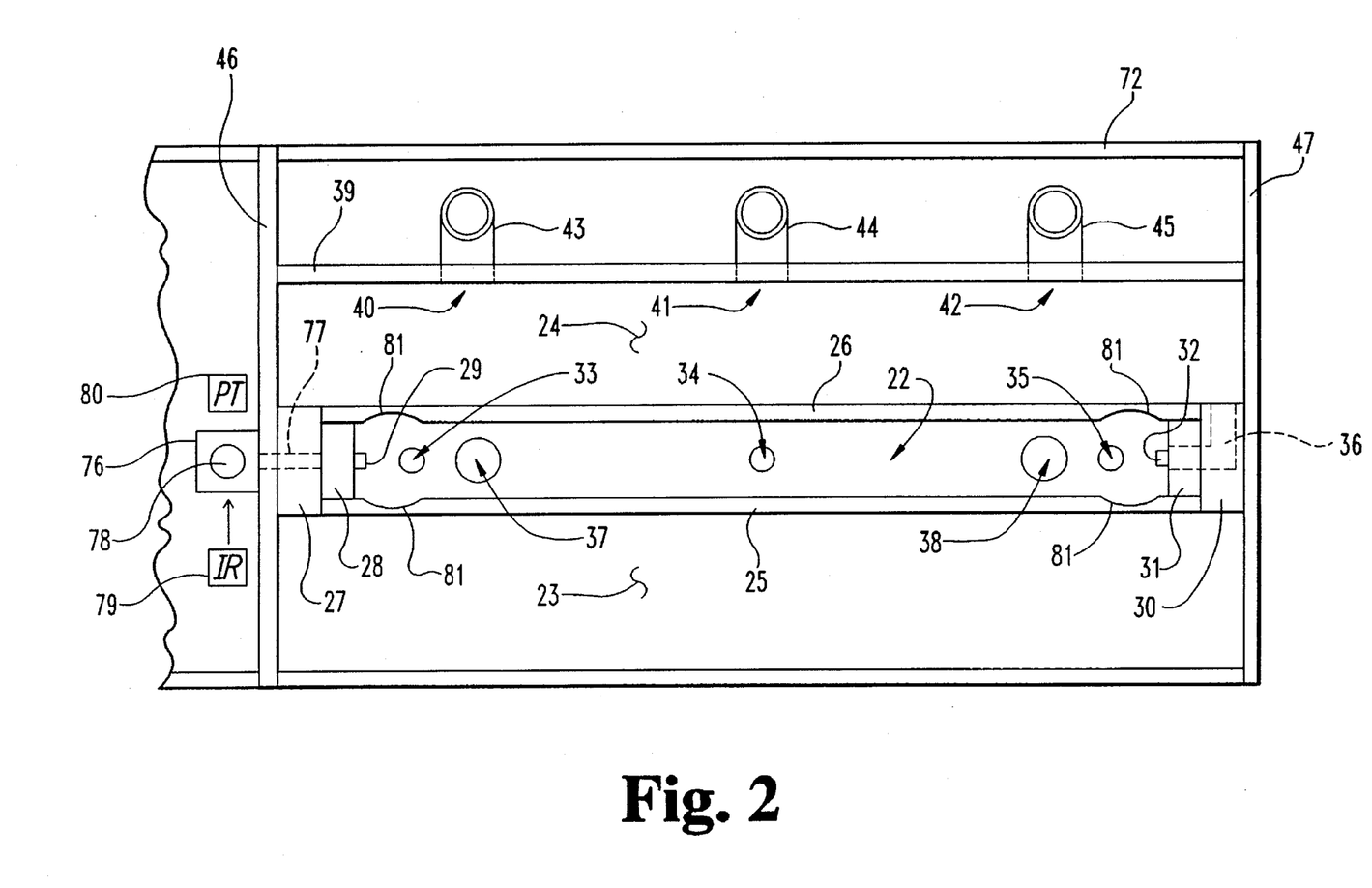
FIG. 2 provides a top view of the gel processing module of the apparatus of FIG. 1 having lid components removed.
Figure 3:
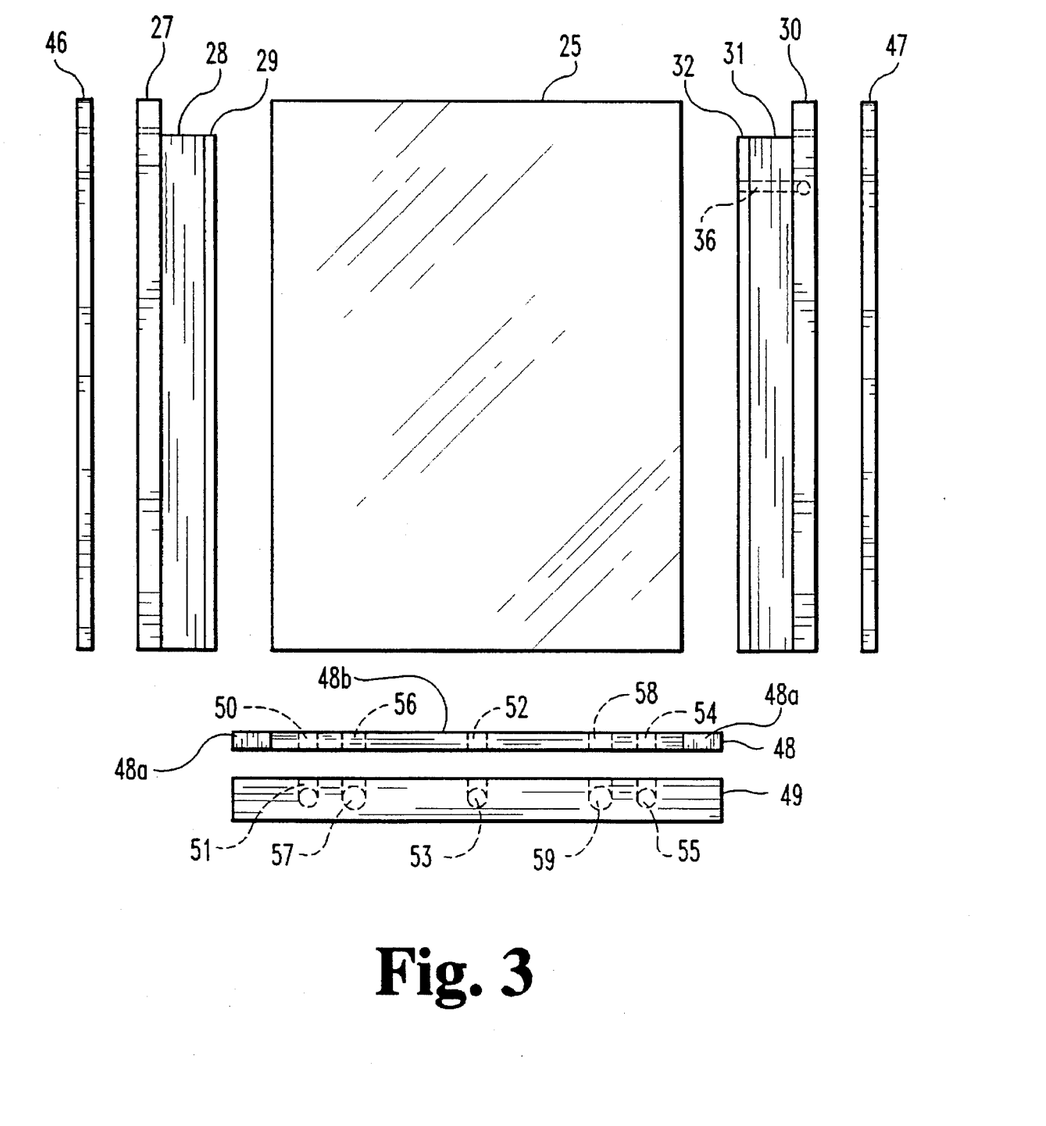
FIG. 3 provides an exploded view of components of the liquid processing chamber of the apparatus of FIG. 1.
Figure 4:
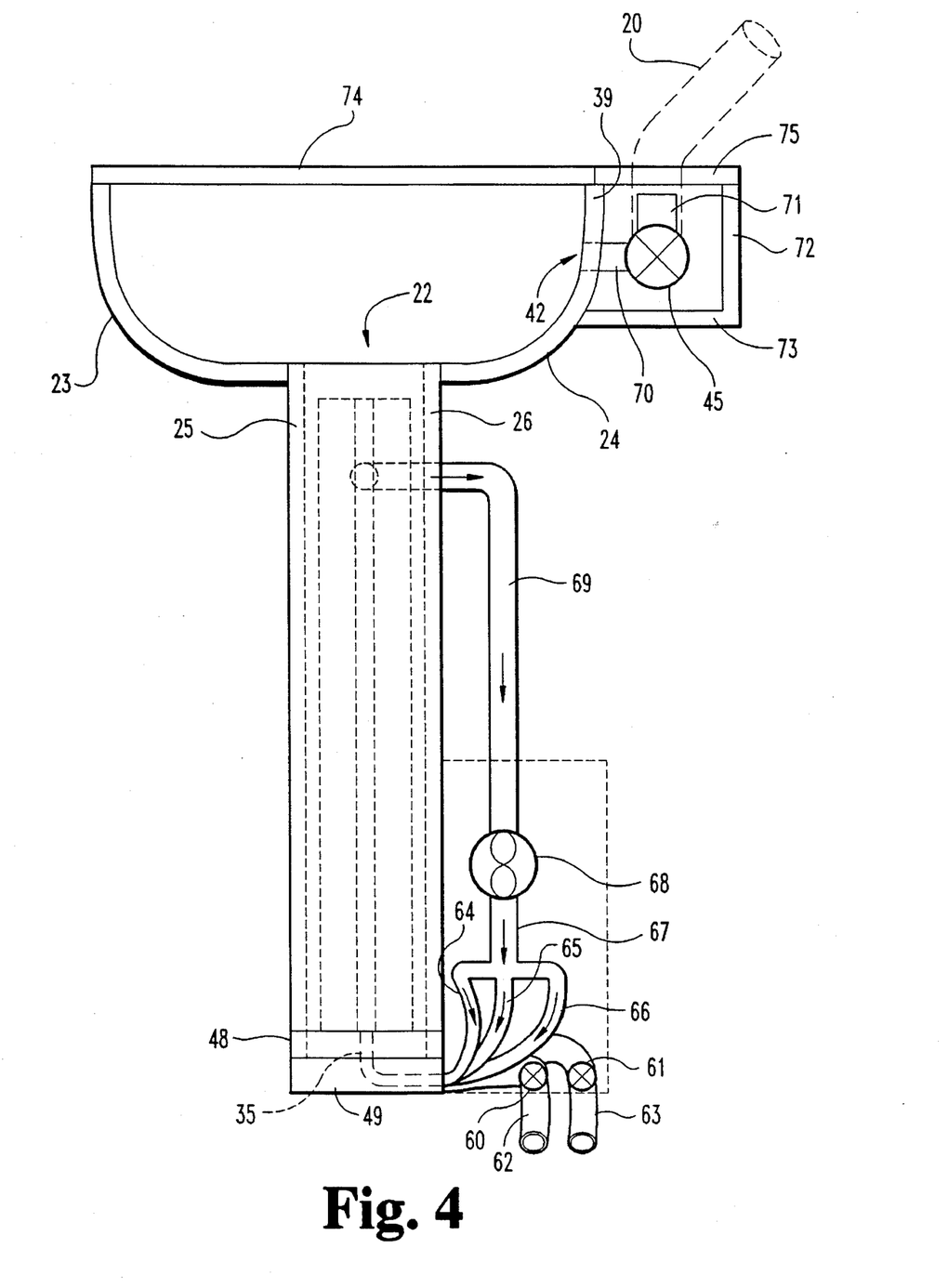
FIG. 4 provides a right side view of the apparatus of FIG. 1 having the right side cover piece removed.

Referring now to FIGS. 2–4, provided are views which illustrate components of liquid processing center 14 of apparatus 11. Liquid processing center 14 includes a relatively deep liquid processing chamber 22 for receiving electrophoresed gels to be processed and a generally wider upper chamber formed by curved members 23 and 24 which upper chamber facilitates the communication of processing solutions down into chamber 22 to contact the electrophoresed gels. Elongate curved members 23 and 24 are bonded to the uppermost outer surfaces of front and back panels 25 and 26, respectively, which form the front and back walls of chamber 22. The side walls of chamber 22 are provided by elongate rectangular side members 27 and 28 (left side) and 30 and 31 (right side). Side members 28 and 31 are bonded to the inner surfaces of members 27 and 30, respectively, and are generally smaller in width than members 27 and 30. In this fashion, shoulders are formed which receive the outermost edges of panels 25 and 26, as illustrated best in FIG. 2. A horizontal bore extends completely through side member 31 and is in fluid communication with an elbow-shaped bore opening at the upper surface of piece 30 and exiting out the back surface of piece 30, to provide liquid recirculation exit port 36. Recirculation exit port 36 serves in the recirculation of liquid in chamber 22 during liquid processing, as discussed more fully below.

Relatively narrow elongate separation members 29 and 32 are bonded to the inner surfaces of members 28 and 31, respectively, and separate chamber 22 into two slots, each of which can receive an electrophoresed gel plate for simultaneous processing. It will be understood in this regard that chamber 22 could be dimensioned and additional separation members provided to form more than two slots and thus enable the processing of more than two gels simultaneously, if desired.

Liquid recirculation entry ports 33, 34 and 35 are provided at the bottom of chamber 22 and serve in the circulation of processing solutions in chamber 22 as described more fully below. Drain holes 37 and 38 are also provided at the bottom of chamber 22 for draining processing solutions after completion of their respective functions in the staining process.

To provide feed of processing solutions to chamber 22, holes 40, 41 and 42 are defined in vertical wall 39 of curved member 24. Solenoid input valves 43, 44 and 45 are mounted to the outside of wall 39. Input valves 43, 44 and 45 each have a horizontally extending output tube member and a vertically extending input tube member. This is illustrated for valve 45 in FIG. 4, which shows horizontal output tube member 70 and vertical input tube member 71. The horizontal outputs of input valves 43, 44 and 45 are aligned with holes 40, 41 and 42 to enable feed of processing solutions through wall 39 whereafter the solutions are communicated by gravity flow into chamber 22.

Liquid processing center 14 has side walls 46 and 47 which are bonded to the outermost edges or surfaces of curved members 23 and 24 and side members 27 and 30. Side walls 46 and 47 are also bonded to the outermost edges of back wall 72 which, along with bottom wall 73 (FIG. 4) encases input valves 43, 44 and 45.

With continued reference to FIGS. 2–4, the bottom of liquid processing center 14 is formed from a generally "T"-shaped upper piece 48 and a rectangular lower piece 49. Upper piece 48 has a central member 48b connecting two generally wider end members 48a. Central member 48b has a length slightly greater than the width of front and back panels 25 and 26. In this fashion, when upper piece 48 is bonded to the upper surface of lower piece 49, shoulders are formed which receive the lowermost edges of panels 25 and 26. Upper piece 48 has relatively smaller diameter bores 50, 52 and 54 extending vertically completely through upper piece 48, which are in registry with elbow-shaped bores 51, 53 and 55 in lower piece 49, respectively. Bores 51, 53 and 55 include vertical bores extending partially through lower piece 49, which meet and fluidly communicate with horizontal bores extending out the back side of lower piece 49. Similar, slightly larger bores are present in upper piece 48 (56, 58) and in lower piece 49 (57, 59). The bores in pieces 48 and 49 together form the recirculation entry ports 33, 34 and 35 and the drain holes 37 and 38 which open at the bottom of chamber 22 and exit out of the back of module 12 for convenient hose attachment.

Describing more particularly the fluid handling aspects of apparatus 11, solenoid drain valves 60 and 61 (FIG. 4) have their inputs fluidly connected to the outlets of drain holes 37 and 38 at the back of module 12. Drain hoses 62 and 63 are connected to the outputs of solenoid drain valves 60 and 61, respectively, which are normally closed but can be energized to an open state to allow drainage. Hoses 64, 65 and 66 are connected to outlets of recirculation ports 35, 34 and 33 on the back of module 12, respectively. Hoses 64, 65 and 66 are merged into a single hose 67 which is fluidly connected to the output of recirculation pump 68. Hose 69 fluidly connects the input of recirculation pump 68 to the outlet of recirculation exit port 36. In this manner, pump 68 can be energized to draw liquid from chamber 22 via liquid exit 36 (flow in direction of arrows) and reintroduce the liquid into chamber 22 via recirculation entry ports 33, 34 and 35. Such liquid recirculation enhances performance of apparatus 11 in the various processing steps required in gel staining protocols. It will be understood that other recirculation routes could also be used, e.g. recirculation from the bottom of chamber 22 to the top. However, recirculation from top to bottom as in the illustrated device is particularly convenient for recirculation line clearance operations following chamber drainage, in that residual solutions in the recirculation lines are pumped to the bottom of chamber 22 for drainage. If a bottom to top recirculation pattern is used, then absent the use of a bi-directional pump, clearance of the recirculation lines would involve transport of the residual solutions to the top of chamber 22 whereupon additional contact with the gels and/or drainage time would result.

As previously indicated, liquid flow into chamber 22 is controlled by solenoid input valves 43, 44 and 45. Valves 43–45 are normally closed but, like valves 60 and 61, can be energized to an open state, to allow passage of liquid into chamber 22. Valves 43, 44, 45, 60 and 61 are preferably high flow valves such as those commercially available from Eaton Corp., Morton Grove, Ill., under part number S50. Liquid from containers 15, 16 and 17 is preferably gravity fed to the input of valves 43, 44 and 45 via hoses 18, 19 and 20.

Generally, in the operation of apparatus 11, one or more of input valves 43, 44 and 45 is energized at an appropriate time and for a sufficient duration to input a first processing liquid, e.g. a fixing solution, into chamber 22. The processing liquid is then recirculated, continuously or periodically, by continuously or periodically energizing recirculation pump 68. After completion of the first processing liquid phase, drain valves 60 and 61 are energized and the liquid allowed to drain under the force of gravity from chamber 22. In this regard, drain valves 60 and 61 preferably have a high flow-through capacity to enable rapid drain of processing liquid from chamber 22. In this manner, uniformity of processing is maintained by ensuring that all areas of the processed gels are contacted with the processing solution for substantially the same period of time. This uniform processing, along with effective recirculation of processing liquids, provides excellent reproducable results, even when processing DNA gels which are known to be highly sensitive to processing variations. Recirculation pump 68 is then energized for a sufficient period to ensure that all lines are free of the first processing liquid. A second processing liquid, e.g. a rinsing solution such as water, is then provided to chamber 22 by energizing the input valve 43, 44 or 45 associated with that liquid. The recirculation, drain and line-clearing functions are then repeated. Additional processing liquids can then be provided and recirculated in and drained from chamber 22 in a similar fashion.

Additional structural components of the gel processing module 12 include removable lid 74 spanning the chamber created by curved pieces 23 and 24. Lid 74 can be removed or otherwise moved (e.g. pivoted) to allow the manual insertion of gels down into chamber 22. Lid piece 75 covers the box formed by walls 39, 72 and 73 and encasing input valves 43–45.

Gel processing module 12 also includes a liquid level sensor for sensing when chamber 22 is full of processing liquid. The liquid level sensor is provided in the preferred apparatus by a clear, liquid tight box 76 (FIG. 2) fluidly coupled to chamber 22 near the top of chamber 22 via bore 77 extending through side piece 27 and into box 76. A float ball 78 is encased in box 76 and constructed of a material generally impenetrable to infrared light, e.g. a colored material. An infrared light source 79 is provided and directs a beam of infrared light through the upper portion of box 75. A phototransistor is mounted on the side of box 75 opposite the location of IR light source 75, and positioned in the path of the IR beam passing through box 75. In this fashion, when chamber 22 is nearly full with processing liquid the liquid will flow through bore 77 and into box 76. As box 76 is then filled with the processing liquid, float ball 78 will be transported to the top of box 76 and thus in the path of the IR beam from IR source 79. The IR beam will thus cease to impinge upon the phototransistor 80, creating a signal that chamber 22 is full. This signal is transmitted to the controlling software which automatically de-energizes and closes the input valve involved, as discussed more fully below.

To facilitate insertion and removal of gels into and from chamber 22, notches 81 are formed into interior of plates 25 and 26 near their outer edges. In this manner, clearances are provided for an operator's fingers to more readily grasp gel plates during their insertion or removal.

Drain ports are also provided in areas of apparatus 12 in which electrical components are present to decrease any risk of flooding of those areas, which could cause equipment damage and pose electrical hazards. For example, the box encasing valves 43, 44 and 45, described above has a drain port in or near its bottom wall to prevent collection of liquids in the box. As well, wiring extending from electronics tower 13 into that box enters through a hole (not shown) in side piece 46 located at an elevation above the drain port. This prevents any liquid collecting in the box from flooding over into electronics tower 13, which could cause equipment damage. As well, the entire apparatus 11 can be bonded or otherwise attached to a broad base, e.g. a section of plexiglass, to stabilize apparatus 11 against accidental tilting or tipping.

The control panel of apparatus 11 includes a plurality of buttons or switches 82, by which an operator can signal the control sequencing software to begin an operation, e.g. to signal initiation of the overall staining routine or accept a selection prompted on liquid crystal display 84. The control panel of apparatus 11 also preferably includes several light emitting diodes (LED's) 83 (FIG. 1), each of which corresponds with a respective input or drain valve and is energized simultaneously with its corresponding valve. The activity of the valves can thus be visually monitored. A power source is also provided to energize the electrical components of apparatus 11 and can be, for example, power derived from a standard electrical outlet via plug 85.

A preferred staining process for use in the present invention is the silver staining process. In accordance with the invention a silver staining process can include cycles including fixing, rinsing, staining, rinsing, developing, stop develop, and rinsing cycles. When using a silver stain, the container (e.g. 16) containing the stain is preferably impenetrable to light, so as to minimize degradation.

The fix cycle utilizes a suitable fixing solution which promotes a covalent boding or other interaction between the biological material and the gel. The fix cycle will typically have a duration of about one to twenty minutes, more preferably about ten minutes. Suitable fixing agents are well known and include, for example, aqueous or alcoholic solutions of organic acids. Suitable organic acids include monobasic carboxylic acids such as acetic acid and propionic acid, dibasic acids such as succinic and tartaric acids, and tribasic acids such as citric acid. Representative alcohols which can be used include lower (i.e. $C_1$ to $C_4$) alcohols, e.g. methanol, ethanol, n-propanol, isopropanol, n-, iso-, sec- or tert-butyl alcohol, and the like. Aqueous solutions of organic acids, especially about 10% acetic acid, are preferred for use in the present invention.

The rinsing solution utilized after the fix cycle can be any liquid which effectively rinses unwanted materials from the gels and the components of apparatus 11. Water, lower alcohols, or their mixtures are common rinse agents and can be employed in the present invention. Deionized water has proven suitable and is a preferred rinse agent in the present invention. It is preferred to conduct at least two rinse cycles after fixing (i.e. contacting the gels with at least two separate aliquots of rinsing solution), more preferably at least three rinse cycles. The duration of the post-fix rinse cycles may vary from several seconds to several minutes. More typically, a post-fix rinse cycle of about 1 to 2 minutes will be used. Additionally, the rinsing solution will be periodically or continuously recirculated during the rinse cycles by appropriate energization of recirculation pump 68.

Suitable silver staining solutions for use in the invention will include a source of silver ions, typically about a 0.5 to 5 g/l aqueous solution of a silver salt which dissociates in water to provide free silver ions. A 1 g/l aqueous silver nitrate ($AgNO_3$) solution is preferred for use in the invention. The silver staining solutions can also contain other conventional ingredients, for example ammonia, primary amines such as methylamine or ethanolamine, or caustic materials such as NaOH or KOH. The duration of the stain cycle will depend upon the stain intensity desired. Typical durations will be from several minutes to about an hour, with about one-half hour usually being suitable.

The post-stain rinse can be conducted using a solution such as those identified for the post-fix rinse above. Again, deionized water has proven suitable and is preferred. One rinse cycle post staining, with continuous or periodic recirculation, has proved suitable to remove excess stain in the applicants' preferred apparatuses and methods; however, additional rinse cycles could be conducted if desired. The post stain rinse cycle can be fairly brief, on the order of less than a minute, but durations of at least about 10 seconds are preferred.

The developing solution for the silver stain will be capable of reducing silver ions to silver metal. Such developing solutions typically include aqueous solutions of bases, for example potassium hydroxide, sodium hydroxide, potassium carbonate or sodium carbonate, in combination with aldehydes such as formaldehyde, acetaldehyde, n-butyraldehyde or glutaraldehyde, and are preferably stored at cool temperature, e.g. under refrigeration. An aqueous solution of sodium carbonate (30 g/liter) and formaldehyde (1.5 ml 37% HCOH/liter) is a preferred developing solution for use in the invention. The duration of the developing cycle will depend upon the stain intensity desired, but will typically have a duration of about 1 to 10 minutes, more typically about 2 to 5 minutes. As with other cycles, it is preferred to recirculate the developer continuously or periodically during the developing cycle.

Once the desired stain intensity has been achieved and the developing cycle is completed, a stop develop cycle will be run. The action of developing agents such as those noted above is terminated upon acidification, and thus the stop developing cycle will usually employ an aqueous acidic solution. In the present invention, when an aqueous organic acid is used as the fixing solution, it can be used to stop development, either alone or optionally diluted with water (e.g. suitable amounts of both fixing solution and rinse water can be fed to chamber 22 to terminate development). The stop develop cycle will be conducted sufficiently to terminate further reduction of the silver ions to silver metal. This is typically accomplished in one cycle, with recirculation, and which can have duration of about 1 to 5 minutes and typically about 2 minutes.

One or more rinse cycles, with recirculation, can be conducted after completion of the stop develop cycle. Rinse agents such as those defined above are suitable, with water again being preferred. It is preferred to conduct two or more rinse cycles to ensure complete removal of residual materials from the gel and apparatus, each of which can have a duration of several seconds to several minutes, more typically lasting for about 1 to 2 minutes. After this final rinse, the gel staining is complete and the gels can be further processed or analyzed in a conventional fashion.

Figure 5:
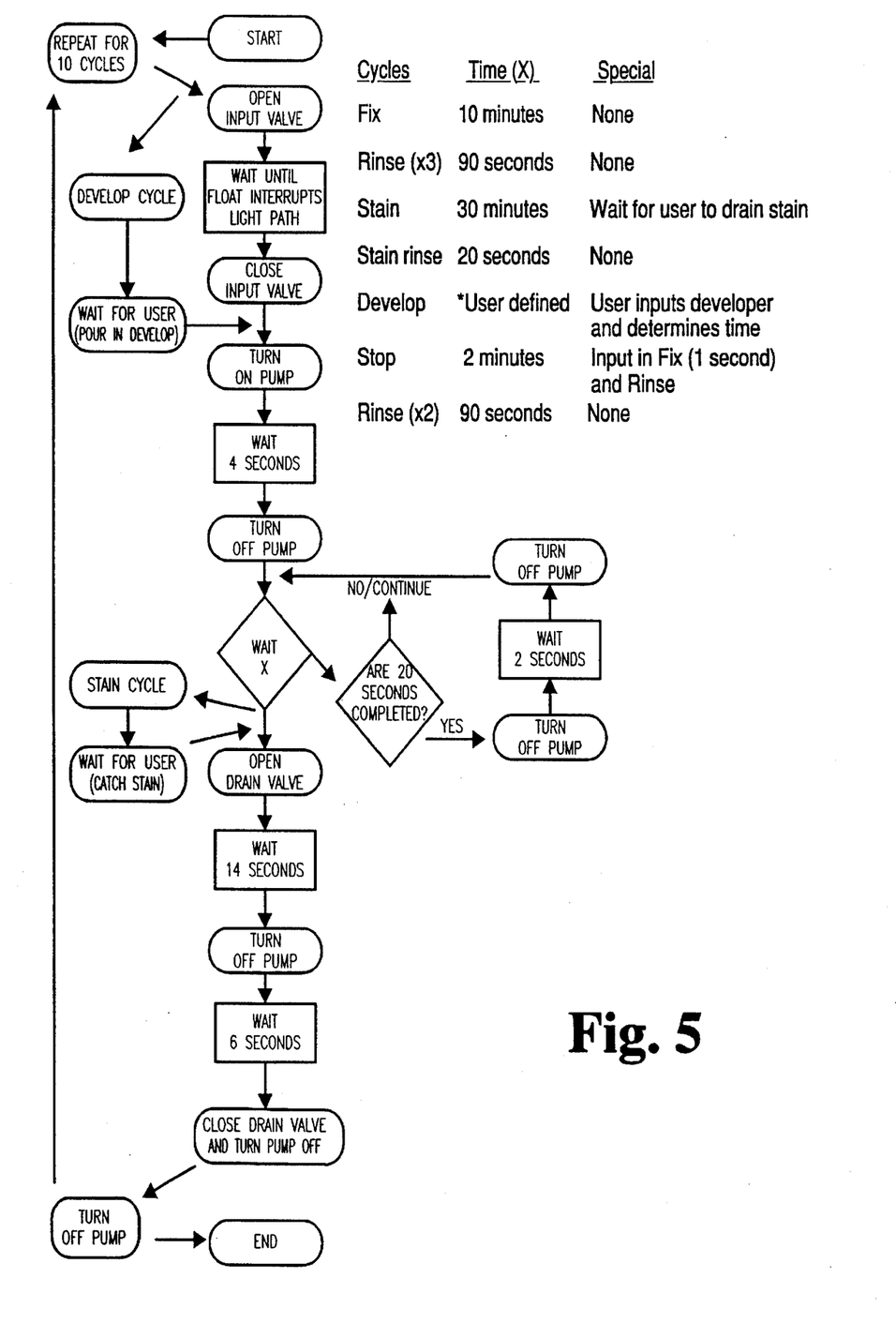
FIG. 5 provides a flow chart illustrating control sequencing software for the apparatus of FIG. 1.

With reference now also to FIG. 5, one example of an automated staining apparatus and procedure of the invention will be given. In particular, FIG. 5 provides a flow chart illustrating control sequencing software for the preferred apparatus 11 which, in association with a microprocessor, is adapted to automate a silver staining process such as that described above. Control sequencing software can be suitably stored in an electronic memory device such as a ROM or an E-prom device, and associated in a conventional fashion with a clock, circuitry and a control panel for user interface to achieve the various automated functions of apparatus 11.

In using apparatus 11, the user places two electrophoresed gels which are chemically affixed to glass plates, for instance affixed with a silane coupling agent, into chamber 22. In so doing, one such gel is positioned on each side of separation members 29 and 32, which sufficiently space the gels from one another to allow effective processing.

As shown in FIG. 5, in the preferred embodiment a start signal is then given, for example by pressing a button on the control panel (e.g. one of buttons 82, FIG. 1). The program is thus initiated. Input valve 43 is automatically energized and thus opened, allowing gravity feed of fixing solution from container 15 into chamber 22. When chamber 22 is filled with fixing solution as signaled by the interruption of the IR light path of the liquid level sensor (FIG. 2, components 76, 78, 79 and 80), input valve 43 is closed to interrupt the flow of fixing solution. Recirculation pump 68 is automatically turned on for a four-second period, and then automatically turned off. A cycle then commences which has a duration dependent upon which processing step is underway. In the fixing cycle this duration is 10 minutes, during which the recirculation pump is turned on every twenty seconds for a period of two seconds. After completion of the 10 minute fixing cycle, drain valves 60 and 61 are automatically opened and the fixing solution drains from liquid chamber 22 and out drain hoses 62 and 63 under the force of gravity. Drain valves 60 and 61 remain open for a period sufficient to drain the fixing solution from chamber 22 (14 seconds), whereafter recirculation pump 68 is automatically turned on for a brief period (6 seconds) to clear the recirculation lines of fixing solution. At this point, drain valves 60 and 61 are automatically closed and pump 68 automatically turned off. The program then proceeds to an end/repeat logic, and after the fixing cycle repeats except employing the rinsing solution.

Thus, the program automatically opens input valve 45 through which rinsing solution (deionized water) is gravity fed to chamber 11. The fill, recirculation, drain and line-clearing functions described above for the fixing cycle are then repeated, except the cycle time (X) is 90 seconds rather than 10 minutes. This rinse cycle is repeated a total of three times.

After the rinse cycle is completed, the automated stain cycle is carried out. The fill and recirculation functions are repeated as above, except the cycle time (X) is 30 minutes. The drain function, however, is not automatically repeated. Instead, in the preferred apparatus 11, the stain is collected and reused, and thus an audio and/or visual signal is given indicating completion of the 30 minute stain cycle. The audio signal may be given, for example, by automatically energizing a piezoelectric buzzer. A visual signal to collect the stain can be given on a two-line, twenty-eight character LCD display 84 provided on the control panel. With drain hoses 62 and 63 positioned in an appropriate collection container, the user then manually depresses one of buttons 82 assigned to signal readiness of the user to collect stain, and the program then continues as described above.

Following the stain cycle, another rinse cycle is automatically carried out, for a duration of 20 seconds. After completion of this rinse cycle, the user removes lid 74 and manually pours the developing solution into chamber 22. It will be understood that the developing solution could be provided in a fourth container and automatically fed to liquid processing center 14. For example, when using a developing solution requiring refrigeration, a refrigerated container could be provided.

After manual feed of the developing solution, the user then replaces lid 74 and depresses one of buttons 82 on the control panel to signal that the developer is in chamber 22. The program then continues with its automatic recirculation, which during the developing cycle assists in preventing localized heat buildup resulting from the chemical interaction of the developer and the stain. During this period, the user visually observes the development of the stain through clear front panel 25. When the desired stain intensity has been achieved, the user manually depresses one of buttons 82 on the control panel to signal the completion of development whereupon the program continues on to its drain, and line-clearing functions.

Next, a stop development cycle is automatically initiated. For the stop cycle in the preferred apparatus 12, input valve 43 is automatically opened for one second to gravity feed a small amount of fixing solution (an aqueous organic acid solution) into chamber 22. Input valve 45 is then opened, thus feeding rinse solution (deionized water) to chamber 22. The fill, recirculate, and drain functions are repeated as described above, with a cycle duration (X) of 2 minutes.

After the stop develop cycle, 2 rinse cycles are automatically carried out as above, each one and one-half minutes in duration. The program thereafter ends, and the gels are stained, developed and ready for further processing and/or analysis.

The control sequencing software can also provide a cleansing cycle for periodic cleansing of apparatus 11. For example, the software can control the addition, recirculation and drainage of an appropriate cleanser and/or neutrilizer contained in further container(s) fluidly connected to liquid processing center 14 in a fashion similar to containers 15–17. Alternatively, the software can be configured to accept signals after manual addition of cleansing materials, and thereupon control recirculation and/or drainage of the materials. As well, the software can be configured to allow a manual mode in which operation of input and drainage valves is controlled by depressing corresponding buttons 82 on the control panel.

While the invention has been illustrated and described in detail in the drawings and foregoing description, the same is to be considered as illustrative and not restrictive in character, it being understood that only the preferred embodiment has been shown and described and that all changes and modifications that some within the spirit of the invention are desired to be protected.

What is claimed is:

1. An apparatus for staining electrophoretic gels, comprising:

a liquid processing chamber sized to receive one or more electrophoretic gels having electrophoresed biological material deposited thereon, said liquid processing chamber being adapted to contain a series of processing fluids in intimate contact with areas of the electrophoretic gels containing the biological material;

a first fluid source containing fixing solution effective to fix the stained biological material, the first fluid source being operable to begin and cease communication of the fixing solution to the liquid processing chamber;

a second fluid source containing staining solution effective to stain the biological material, the second fluid source being operable to begin and cease communication of the staining solution to the liquid processing chamber;

a third fluid source containing rinsing solution, the third fluid source being operable to begin and cease communication of the rinsing solution to the liquid processing chamber;

at least one drain in the liquid processing chamber having an open state for draining staining solution, developing solution and rinsing solution from the liquid processing chamber, and a closed state for retaining the staining solution, developing solution and rinsing solution in the liquid processing chamber;

control sequencing software operable to control said first, second and third fluid sources and said drain so as to achieve serial contact of the electrophoretic gel plates with the fixing solution, staining solution, and rinsing solution;

a recirculation pump having an input and an output each in fluid communication with said chamber, said recirculation pump being operable to circulate processing solutions in said chamber.

2. The automated apparatus of claim 1, wherein:

said first, second and third fluid sources include:
first, second and third containers containing, respectively, said fixing, staining and rinsing solutions; and
first, second and third input valves having inlets in fluid communication with said first, second and third containers and outlets in fluid communication with said liquid processing chamber, said valves being normally closed but opening when energized;

said drain includes a drain valve which is normally closed but which opens when energized; and wherein said apparatus also comprises a power source for energizing said input valves and said drain valve at selected times, the power source being controlled by said software to energize said input valves and drain valve so as to achieve serial contact of the electrophoretic gel plates with the fixing solution, staining solution, and rinsing solution.

3. The apparatus of claim 2 wherein said first, second and third fluid sources are positioned to enable gravity feed of said solutions to the liquid processing chamber, and said drain is positioned to enable gravity drain of said solutions from the liquid processing chamber.

4. The apparatus of claim 3, additionally comprising:

at least one recirculation exit port from said chamber in fluid communication with the pump input and at least one recirculation entry port into said chamber in fluid communication with the pump output; and wherein said recirculation pump is operable upon energization to draw processing solutions from the exit port and pass them into the entry port to circulate processing solutions in said chamber; and wherein said sequencing software controls energization of said recirculation pump to circulate processing solutions in said chamber at selected times.

5. The apparatus of claim 1 wherein said liquid processing chamber is sized to receive two or more electrophoresed gels.

6. The apparatus of claim 5 wherein:

said fixing solution is an aqueous solution of an organic acid;

said stain is a silver stain containing a source of silver ions;

said rinsing solution is water; and wherein said sequencing software is operable to control said valves so as to automatically serially contact the gels with (i) said fixing solution, (ii) said rinsing solution, (iii) said silver stain, and (iv) said rinsing solution, and to automatically control said recirculation pump to recirculate the solutions in steps (i)–(iv).

7. The apparatus of claim 6 wherein:

said software is operable to initiate the energization of an audio and/or visual signal after rinse step (iv), whereby a user is informed that step (iv) is complete and can manually fill said liquid processing chamber with a developing solution capable of reducing the silver ions to silver metal.

8. The apparatus of claim 7, wherein:

said sequencing software is adapted to be signaled by a user after manually filling said liquid processing center with the developing solution, and thereupon to control energization of said recirculation pump to recirculate the developing solution in said liquid processing chamber.

9. The apparatus of claim 8, wherein:

said sequencing software is adapted to be signaled by a user after the developing solution has been recirculated in said chamber for a period of time sufficient to develop the silver stain, and thereupon to control energization of said drain valve to automatically drain the developing solution from said liquid processing chamber.

10. The apparatus of claim 9, wherein:

said sequencing software is operable to control energization of said input valves and drain valve after the developing solution is drained from said liquid processing chamber, so as to automatically contact the gels with a develop stop solution comprising a mixture of said fixing solution and said rinsing solution, and automatically drain said mixture from the liquid processing chamber.

11. The device of claim 10, wherein:

said sequencing software is operable to control energization of said input valves and said drain valve after said mixture is drained from the liquid processing chamber, so as to automatically contact the gels with said rinsing solution.

12. A process for staining electrophoretic gels, comprising:

placing one or more electrophoretic gels having elecrophoresed biological material deposited thereon into a liquid processing chamber sized to receive the electrophoretic gels, the liquid processing chamber being adapted to contain a series of processing fluids in intimate contact with areas of the electrophoretic gel plates containing the biological material;

providing a first fluid source containing fixing solution effective to fix the stained biological material, the first fluid source being operable begin and cease communication of the developing solution to the liquid processing chamber;

providing a second fluid source containing staining solution effective to stain the biological material, the second fluid source being operable begin and cease communication of the staining solution to the liquid processing chamber;

providing a third fluid source containing rinsing solution, the third fluid source being operable to begin and cease communication of the rinsing solution to the liquid processing chamber;

providing a drain in the liquid processing chamber having an open state for draining fixing solution, staining solution, and rinsing solution from the liquid processing chamber, and a closed state for retaining the staining solution, developing solution and rinsing solution in the liquid processing chamber;

providing a recirculation pump having an input and an output each in fluid communication with said chamber, said recirculation pump being operable to circulate processing solutions in said chamber;

providing control sequencing software operable to control said first, second and third fluid sources and said drain so as to serially contact the electrophoretic gels with the fixing solution, staining solution, and rinsing solution; said software also being operable to control energization of said recirculation pump to circulate processing solutions in said chamber at selected times; and initiating the control sequencing software so as to cause the liquid processing chamber to be filled with and then drained of the fixing solution, staining solution, and rinsing solution in a serial fashion under control of the control sequencing software, and to cause energization of said recirculation pump to circulate processing solutions in said chamber at selected times.

13. The process of claim 12 wherein:

the fixing solution is an aqueous solution of an organic acid;

the staining solution is a silver staining solution containing a source of silver ions;

the rinsing solution is water; and wherein the sequencing software controls the valves so as to fill and drain the liquid processing chamber with and of (i) said fixing solution, (ii) said rinsing solution, (iii) said silver staining solution, and (iv) said rinsing solution.

14. The process of claim 13 wherein:

step (i) includes filling the chamber with the fixing solution for a duration of about 1 to 10 minutes, and then draining the fixing solution; step (ii) includes filling and draining the chamber at least three times with said rinsing solution; and step (iii) includes filling the chamber with the staining solution, and draining the staining solution after a duration of up to one hour; and step (iv) includes filling the chamber with the rinsing solution, and draining the rinsing solution after a duration of at least 10 seconds.

15. The process of claim 14 wherein after said rinse step (iv), said sequencing software initiates the energization of an audio and/or visual signal, and wherein said process additionally comprises:

manually filling the liquid processing chamber with a developing solution capable of reducing the silver ions to silver metal; and signalling the sequencing software after a period of time sufficient to achieve development of the silver staining solution.

16. The process of claim 15, wherein in response to said signalling, said sequencing software is adapted to control energization of said input valves and drain valve to:

drain the developing solution from the liquid processing chamber;

contact the gels with a develop stop solution comprising a mixture of said fixing solution and said rinsing solution; and automatically drain said mixture from the liquid processing chamber; and then automatically contact the gels with the rinsing solution.

17. The process of claim 16 wherein said biological material comprises DNA.

18. A method for processing of electrophoretic gels, comprising:

(i) placing one or more electrophoretic gels having elecrophoresed biological material deposited thereon into a liquid processing chamber sized to receive the electrophoretic gels;

(ii) filling and then draining the liquid processing chamber with and of a fixing solution effective to fix the biological material, the fixing solution intimately contacting areas of the electrophoretic gel containing biological material;

(iii) filling, recirculating and then draining the liquid processing chamber with and of a rinsing solution effective to rinse residual fixing solution from the gel and liquid processing chamber, the rinsing solution intimately contacting areas of the electrophoretic gel containing biological material;

(iv) filling and then draining the liquid processing chamber with and of a silver staining solution effective to stain the biological material, the staining solution intimately contacting areas of the electrophoretic gel containing biological material;

(v) filling, recirculating and then draining the liquid processing chamber with and of a rinsing solution effective to rinse the electrophoretic gel and liquid processing chamber of residual staining solution, the rinsing solution intimately contacting areas of the electrophoretic gel containing biological material;

(vi) filling and recirculating the liquid processing chamber with a developing solution effective to develop the stained biological material, the developing solution intimately contacting areas of the electrophoretic gel containing stained biological material;

(vii) draining the developing solution from the liquid processing chamber; and (viii) filling and then draining the liquid processing chamber with and of a stop develop solution effective to stop development of the gel by the developing solution; and (ix) filling and then draining the liquid processing chamber with and of a rinsing solution.

19. The process of claim 18 wherein:

at least steps (ii), (iii), (iv), (v), (vii), (viii) and (ix) are performed in response to the operation of control sequencing software.

20. The process of claim 19, also including recirculating the rinsing solutions during their residence in the chamber in steps (ii), (iv) and (viii).

21. The process of claim 20 wherein:

the fixing solution is an aqueous solution of an organic acid;

the rinsing solutions are each water;

the silver staining solution is silver nitrate; and the developing solution is aqueous solution of an organic acid.

22. The process of claim 21 wherein said biological material comprises DNA.

* * * * *